US010995142B2

(12) United States Patent
Xu et al.

(10) Patent No.: US 10,995,142 B2
(45) Date of Patent: May 4, 2021

(54) MONOCLONAL ANTIBODY FNAB8 AND APPLICATION THEREOF

(71) Applicant: Shanghai Jiaotong University, Shanghai (CN)

(72) Inventors: Yuhong Xu, Shanghai (CN); Yangsheng Qiu, Shanghai (CN)

(73) Assignee: Shanghai Jiaotong University, Shanghai (CN)

( * ) Notice: Subject to any disclaimer, the term of this patent is extended or adjusted under 35 U.S.C. 154(b) by 110 days.

(21) Appl. No.: 16/069,423

(22) PCT Filed: Jan. 11, 2017

(86) PCT No.: PCT/CN2017/070856
§ 371 (c)(1),
(2) Date: Jul. 11, 2018

(87) PCT Pub. No.: WO2017/121330
PCT Pub. Date: Jul. 20, 2017

(65) Prior Publication Data

US 2019/0023785 A1 Jan. 24, 2019

(30) Foreign Application Priority Data

Jan. 11, 2016 (CN) ......................... 201610016502.2

(51) Int. Cl.

| | |
|---|---|
| ***C07K 16/28*** | (2006.01) |
| ***C12N 15/62*** | (2006.01) |
| ***A61K 47/00*** | (2006.01) |
| ***A61K 47/64*** | (2017.01) |
| ***A61K 47/65*** | (2017.01) |
| ***A61P 3/10*** | (2006.01) |
| ***C07K 14/52*** | (2006.01) |
| ***C07K 14/605*** | (2006.01) |
| ***C07K 16/06*** | (2006.01) |
| ***C12N 15/113*** | (2010.01) |
| ***A61K 39/00*** | (2006.01) |

(52) U.S. Cl.
CPC ............ *C07K 16/283* (2013.01); *A61K 47/00* (2013.01); *A61K 47/6425* (2017.08); *A61K 47/65* (2017.08); *A61P 3/10* (2018.01); *C07K 14/52* (2013.01); *C07K 14/605* (2013.01); *C07K 16/065* (2013.01); *C07K 16/28* (2013.01); *C12N 15/113* (2013.01); *C12N 15/62* (2013.01); *C12N 15/625* (2013.01); *A61K 2039/505* (2013.01); *C07K 2317/94* (2013.01); *C07K 2319/00* (2013.01)

(58) Field of Classification Search
None
See application file for complete search history.

(56) References Cited

U.S. PATENT DOCUMENTS

2010/0266530 A1 10/2010 Roopenian et al.

FOREIGN PATENT DOCUMENTS

| | | | |
|---|---|---|---|
| CN | 104364265 | A | 2/2015 |
| JP | 2011523351 | A | 8/2011 |
| JP | 2015525204 | A | 9/2015 |
| WO | 2009131702 | A2 | 10/2009 |
| WO | 2014019727 | A1 | 2/2014 |
| WO | 2015071330 | A1 | 5/2015 |
| WO | 2015167293 | A1 | 11/2015 |
| WO | 2016183352 | A1 | 11/2016 |

OTHER PUBLICATIONS

Bendig (Methods: A Companion to Methods in Enzymology 1995; 8:83-93).*
Colman (Research in Immunology 145: 33-36, 1994).*
Chen et al. (EMBO J., 14:2784-2794, 1995).*
Kussie et al. (J. Immunol. 152: 146-152, 1994).*
Paul, Fundamental Immunology, 3rd Edition, 1993, pp. 292-295, under the heading "Fv Structure and Diversity in Three Dimensions").*
Rudikoff et al (PNAS, USA, Mar. 1982, 79/6:1979-1983).*
Padlan et al (PNAS, USA 1989, 86:5938-5942).*
MacCallum et al. (J. Mol. Biol., 262, 732-745, 1996).*
Casset et al. (Biochemical and Biophysical Research Communications, 307:198-205, 2003).*
Assession No. AZQ80354, Feb. 2, 2012.*
Accession No. ADZ23007, Jun. 16, 2005.*
Robert L. Shields et al., "High Resolution Mapping of the Binding Site on Human IgG1 for FcgRI, FcgRII, FcgRIII, and FcRn and Design of IgG1 Variants with Improved Binding to the FcgR", The Journal of Biological Chemistry, vol. 276, No. 9, Mar. 2, 2001, pp. 6591-6604.
Gregory J. Christianson et al., "Monoclonal antibodies directed against human FcRn and their applications", mAbs, vol. 4, issue 2, Mar./Apr. 2012.
Johan Seijsing et al., "An engineered affibody molecule with pH-dependent binding to FcRn mediates extended circulatory half-lift of a fusion protein", PNAS, Dec. 2, 2014, vol. 111, No. 48, pp. 17110-17115.

* cited by examiner

*Primary Examiner* — Patricia Duffy
(74) *Attorney, Agent, or Firm* — Novick, Kim & Lee, PLLC; Bin Lu; Zhi Yang Xue

(57) ABSTRACT

Provided in the present invention are a monoclonal antibody FnAb8 and application thereof.

15 Claims, 3 Drawing Sheets

Specification includes a Sequence Listing.

MONOCLONAL ANTIBODY FNAB8 AND APPLICATION THEREOF

INCORPORATION OF SEQUENCE LISTING

This application contains a sequence listing submitted in Computer Readable Form (CRF). The CFR file containing the sequence listing entitled "5-SequenceListing.txt", which was created on Jul. 11, 2018, and is 19,938 bytes in size. The information in the sequence listing is incorporated herein by reference in its entirety.

FIELD OF INVENTION

The present invention relates to the field of bio-medicine, in particular, to an FnAb8 monoclonal antibody and use thereof.

BACKGROUND OF INVENTION

FcRn (Neonatal FC receptor) is a homologue of the major histocompatibility complex I (MHC-I). It is a heterogeneous dimer composed of two polypeptide chains. One is a type I transmembrane protein α chain, which consists of extracellular α1, α2, α3 domain, transmembrane regions and intracellular segments. The other is the $\beta_2$-microglobulin chain ($\beta_2$M).

The major function of FcRn is to bind to the Fc fragment of the IgG molecule and serum albumin (SA), which prevents them from going to the protein degradation pathway after being ingested into the cells, thus prolonging their circulation half-life in vivo. Immunoglobulin (IgG) and albumin (serum albumin, SA) are the two most important protein molecules in the human body, account for 80% of the total plasma protein, with 12 and 40 mg/ml concentration respectively. The functions of SA in vivo include transporting various small molecules, maintaining blood pH and osmotic pressure. IgG, as the major antibody subtype, plays an important role in protecting the body from pathogens. IgGs and SAs have half-lives of up to three weeks in vivo, much higher than other proteins, mainly because of their interactions with FcRn which prevents their degradation in the cells.

It's known that FcRn exists in the endosome, IgG and SA in the blood circulation enter the intracellular endosome under the endocytosis of vascular endothelial cells, and FcRn binds to IgG and SA at acidic pH of endosome with a binding affinity between 500 nM and 2000 nM, thereby protecting IgG and SA from further metabolic degradation. IgG and SA return to the cell surface through recycling of endosomes, returning to the cell surface, the affinity is higher than 10 uM at blood neutral pH (i.e., pH 7.4), and IgG and SA dissociate from FcRn and re-enter the blood circulation.

Based on such a mechanism, the circulation properties of IgG and SA mediated by FcRn may be used to prolong the circulating half-life of protein drugs in vivo. For example, Fc or SA fragments were used to be coupled with drugs or proteins by genetic engineering. Or specific ligands that bind strongly to IgGs or SAs were developed and conjugated with drugs by chemical or biological means to extend their half life. Some products using these mechanisms have been developed and marketed, such as the drugs against autoimmune disease, Enbrel and Alprolix.

However, in addition to FcRn binding function, wild-type Fc fragments may bind to other Fc receptors and may induce antibody-mediated cytotoxicity (ADCC). Therefore, the drug-Fc fusion proteins also produce complicate side effects.

Protein-SA encounters similar problem. Researchers have been trying to modify the sequences of Fc segments or SA to improve their pH dependent binding to FcRn in order to obtain sustained plasma concentration in vivo.

The purpose of the pH-related FcRn binding property is to let a drug specifically and high efficiently bind to FcRn in the endosome (pH 6.0-6.5), and when drug-FcRn circulates onto the cell surface (pH 7.2-7.4), there is also a release of the greatest degree. However, there are many factors that affect this effect, and it is difficult to obtain protein molecules having suitable characteristics in the art.

SUMMARY OF INVENTION

One purpose of the invention is to provide an FnAb8 monoclonal antibody and use thereof. The experimental results show that the antibody sequence obtained by the present invention is coupled with protein, polypeptide or other drug molecules, and the half-life and efficacy of the drug can be greatly prolonged through FcRn cycle protection mechanism.

In the first aspect of the invention, a heavy chain variable region of an antibody is provided, wherein the heavy chain variable region has one or more of the following complementary determining regions (CDRs):

CDR1 as shown in SEQ ID NO: 4,

CDR2 as shown in SEQ ID NO: 6 and

CDR3 as shown in SEQ ID NO: 8.

In another preferred embodiment, the heavy chain variable region has the amino acid sequence as shown in SEQ ID NO: 10.

In the second aspect of the invention, a heavy chain of an antibody is provided, wherein the heavy chain has a heavy chain variable region according to the first aspect of the present invention and a heavy chain constant region.

In another preferred embodiment, the heavy chain constant region is of human or mouse.

In the third aspect of the invention, a light chain variable region of an antibody is provided, wherein the light chain variable region comprises complementary determining regions (CDR) selected from the group consisting of:

CDR1' as shown in SEQ ID NO: 14,

CDR2' as shown in SEQ ID NO: 16 and

CDR3' as shown in SEQ ID NO: 18.

In another preferred embodiment, the light chain variable region has the amino acid sequence as shown in SEQ ID NO: 20.

In the fourth aspect of the invention, a light chain of an antibody is provided, wherein the light chain has a light chain variable region according to the third aspect of the present invention and a light chain constant region.

In another preferred embodiment, the light chain constant region is of human or mouse.

In the fifth aspect of the invention, an antibody is provided, wherein the antibody has:

(1) a heavy chain variable region according to the first aspect of the present invention; and/or (2) a light chain variable region according to the third aspect of the present invention.

In another preferred embodiment, the antibody has a heavy chain according to the second aspect of the present invention; and/or the light chain according to the fourth aspect of the present invention.

In another preferred embodiment, the antibody is an antibody specific to FCRN protein.

In another preferred embodiment, the antibody includes: a single chain antibody (scFv), a double chain antibody, a monoclonal antibody, a chimeric antibody (e.g. a human-mouse chimeric antibody), a murine antibody or a humanized antibody.

In the sixth aspect of the invention, a recombinant protein is provided, wherein the protein has:

(i) the sequence of the heavy chain variable region according to the first aspect of the present invention, the sequence of the heavy chain according to the second aspect of the present invention, the sequence of the light chain variable region according to the third aspect of the present invention, the sequence of the light chain according to the fourth aspect of the present invention or the sequence of the antibody according to the fifth aspect of the present invention;

(ii) a polypeptide, protein drug sequence; and (iii) optionally a tag sequence that assists in expression and/or purification.

In another preferred embodiment, the polypeptide protein drug is selected from the group consisting of: insulin, IL-2, interferon, calcitonin, GHRH peptide, gut peptide analog, albumin, antibody fragments, cytokines, and hormones, etc.

In another preferred embodiment, the polypeptide protein drug is a single chain antibody (scFv), a double chain antibody, a monoclonal antibody, or a chimeric antibody.

In another preferred embodiment, the tag sequence is selected from the group consisting of: 6×His tag, GGGS sequence, FLAG tag.

In another preferred embodiment, the recombinant protein includes bispecific antibody, chimeric antibody.

In the seventh aspect of the invention, a polynucleotide is provided, which encodes a polypeptide selected from the group consisting of:

(1) the heavy chain variable region according to the first aspect of the present invention, the heavy chain according to the second aspect of the present invention, the light chain variable region according to the third aspect of the present invention, the light chain according to the fourth aspect of the present invention, the antibody according to the fifth aspect of the present invention; or (2) the recombinant protein according to the sixth aspect of the present invention.

In another preferred embodiment, the polynucleotide has the sequence as shown in SEQ ID NO: 3, 5, 7, 9, 13, 15, 17 or 19.

In the eighth aspect of the invention, a vector is provided, which comprises the polynucleotide according to the seventh aspect of the present invention.

In another preferred embodiment, the vector includes bacterial plasmids, phages, yeast plasmids, plant cell virus and mammalian cell virus, for instance adenovirus, retrovirus or other vectors.

In the ninth aspect of the invention, a genetically engineered host cell is provided, which comprises the vector according to the eighth aspect of the present invention or has a polynucleotide according to the seventh aspect of the invention integrated in its chromosome.

In the tenth aspect of the invention, an immunoconjugate is provided, which comprises:

(a) the heavy chain variable region according to the first aspect of the present invention, the heavy chain according to the second aspect of the present invention, the light chain variable region according to the third aspect of the present invention, the light chain according to the fourth aspect of the present invention, the antibody according to the fifth aspect of the present invention or the recombinant protein according to the sixth aspect of the present invention; and (b) a coupling moiety selected from the group consisting of a detectable label, a drug, a toxin, a cytokine, a radionuclide, or an enzyme.

In another preferred embodiment, the coupling moiety is selected from the group consisting of a fluorescent or luminescent label, a radiolabel, a MRI (magnetic resonance imaging) or CT (computed X-ray tomography) contrast agent, or an enzyme capable of producing detectable products, a radionuclide, a biotoxin, a cytokine (e.g., IL-2, etc.), an antibody, an antibody Fc fragment, a scFv antibody fragment, a gold nanoparticle/nanorod, a virus particle, a liposome, a nano-magnetic particle, a prodrug activating enzyme (e.g., DT-diaphorase (DTD) or a biphenyl hydrolase-like protein (BPHL)), a chemotherapeutic agent (e.g., cisplatin) or a nano-particle in any form.

In the eleventh aspect of the invention, a pharmaceutical composition is provided, which comprises:

(i) the heavy chain variable region according to the first aspect of the present invention, the heavy chain according to the second aspect of the present invention, the light chain variable region according to the third aspect of the present invention, the light chain according to the fourth aspect of the present invention, the antibody according to the fifth aspect of the present invention, the recombinant protein according to the sixth aspect of the present invention, or the immunoconjugate according to the tenth aspect of the present invention; and (ii) a pharmaceutically acceptable carrier.

In another preferred embodiment, the pharmaceutical composition is in the form of an injection.

In the twelfth aspect of the invention, a use of the heavy chain variable region according to the first aspect of the present invention, the heavy chain according to the second aspect of the present invention, the light chain variable region according to the third aspect of the present invention, the light chain according to the fourth aspect of the present invention, the antibody according to the fifth aspect of the present invention, the recombinant protein according to the sixth aspect of the present invention, or the immunoconjugate according to the tenth aspect of the present invention is provided for preparing an agent, a reagent, a detection plate or a kit.

In another preferred embodiment, the reagents include chips, antibody-coated immune-particles.

In the thirteenth aspect of the invention, a preparation method for a recombinant polypeptide is provided, which comprises following steps:

(a) culturing the host cell according to the ninth aspect of the invention under a condition suitable for expression;

(b) isolating the recombinant polypeptide from the culture, wherein the recombinant polypeptide is the antibody according to the fifth aspect of the present invention or the recombinant protein according to the sixth aspect of the present invention.

It should be understood that, within the scope of the present invention, the technical features specifically described above and below (such as in the Examples) can be combined with each other, thereby constituting a new or preferred technical solution which needs not be described one by one.

DETAILED DESCRIPTION OF THE INVENTION

Figure 1:
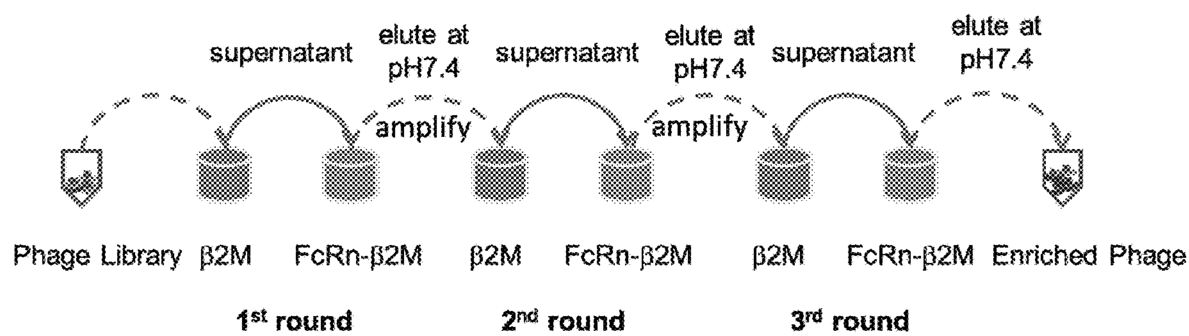
FIG. 1 shows a method for screening a constructed single-chain antibody phage library.

Through extensive and intensive researches, the inventors have discovered a monoclonal antibody which binds to hFcRn. The experimental results show that the sequence obtained by the present invention is coupled with a protein or polypeptide, and the half-life and efficacy of the protein or polypeptide can be greatly prolonged through FcRn cycle protection mechanism.

Before describing the present invention, it should be understood that the invention is not limited to the described particular methodology and experimental conditions, as such methods and conditions may be varied. It is also to be understood that the terminology used herein is only for the purpose of describing particular embodiments, and is not intended to be limiting, and the scope of the invention will be limited only by the appended claims.

Unless otherwise defined, all technical and scientific terms used herein have the same meaning as commonly understood by the ordinary skilled in the art to which this invention belongs. As used herein, the term "about" when used in reference to a particular listed value means that the value can vary from the listed value by no more than 1%. For example, as used herein, the expression of "about 100" includes all values between 99 and 101 (for example, 99.1, 99.2, 99.3, 99.4, etc.).

Although any methods and materials similar or equivalent to those described in this disclosure may be used in the practice or testing of the present invention, the preferred methods and materials are exemplified herein.

FcRn

The monoclonal antibodies of the present invention are against FcRn (neonatal Fc receptor) and have a significant pH-dependent binding to FcRn.

In one aspect of the present invention, a monoclonal antibody is provided, and the monoclonal antibody specifically binds to FcRn, and the binding of the monoclonal antibody to FcRn is pH dependent.

In a preferred embodiment of the invention, if the binding activity of the monoclonal antibody to FcRn is A1 at about pH≥7.0 (preferably ≥7.2, more preferably ≥7.4; most preferably ≥7.6; and pH≤8.5); the binding activity of the monoclonal antibody to FcRn is A2 at about pH≤6.8 (preferably ≤6.6, more preferably ≤6.4; most preferably ≤6.2; and pH≥3.0); then A1/A2≥100 (preferably ≥200, more preferably ≥400; most preferably ≥600; and pH≤10). The binding activity of the monoclonal antibody to FcRn can be detected by conventional methods in the art, as reported in Reference 1.

In a preferred embodiment of the invention, the amino acid sequence of FcRn is:

```
                                                      (SEQ ID NO.: 1)
        10         20         30         40         50
MGVPRPQPWA LGLLLFLLPG SLGAESHLSL LYHLTAVSSP APGTPAFWVS

        60         70         80         90        100
GWLGPQQYLS YNSLRGEAEP CGAWVWENQV SWYWEKETTD LRIKEKLFLE

       110        120        130        140        150
AFKALGGKGP YTLQGLLGCE LGPDNTSVPT AKFALNGEEF MNFDLKQGTW

       160        170        180        190        200
GGDWPEALAI SQRWQQQDKA ANKELTFLLF SCPHRLREHL ERGRGNLEWK

       210        220        230        240        250
EPPSMRLKAR PSSPGFSVLT CSAFSFYPPE LQLRFLRNGL AAGTGQGDFG

       260        270        280        290        300
PNSDGSFHAS SSLTVKSGDE HHYCCIVQHA GLAQPLRVEL ESPAKSSVLV

       310        320        330        340        350
VGIVIGVLLL TAAAVGGALL WRRMRSGLPA PWISLRGDDT GVLLPTPGEA

       360
QDADLKDVNV IPATA
```

Antibody

The term "antibody" or "immunoglobulin" as used herein refers to a heterotetrameric glycoprotein with the same structural feature of about 150,000 daltons, which consists of two identical light chains (L) and two identical heavy chains (H). Each light chain is linked to a heavy chain by a covalent disulfide bond, and the numbers of disulfide bonds between the heavy chains of different immunoglobulin isoforms are different. Each heavy and light chain also has regularly spaced intrachain disulfide bonds. Each heavy chain has a variable region (VH) at one end, followed by a plurality of constant regions. Each light chain has a variable region (VL) at one end and a constant region at the other end; the constant region of the light chain corresponds to the first constant region of the heavy chain; and the variable region of the light chain corresponds to the variable region of the heavy chain. There is an interface formed between the variable regions of the light and heavy chains by particular amino acid residues.

As used herein, the term "variable" means that some certain portions of the variable region of an antibody differ in sequence and contribute to the binding and specificity of each particular antibody to its particular antigen. However, the variability is not evenly distributed throughout the antibody variable region. It is concentrated in three regions in the light and heavy chain variable regions called complementary determining regions (CDRs) or hypervariable regions. The relatively conserved portions of the variable regions are referred as framework regions (FRs). The variable regions of the natural heavy and light chains each comprises four FR regions, which are in a substantially β-folded configuration, and are linked by three CDRs that form the linker ring and, in some cases, form a partial β-folded structure. The CDRs in each chain stand close together through FR regions and form the antigen-binding site of the antibody together with the CDRs of the other chain (see Kabat et al., NIH Publ. No. 91-3242, Vol. I, 647-669 (1991)). Constant regions are not directly involved in the binding of the antibodies to the antigens, but they exhibit different effector functions, such as antibody-dependent cytotoxicity involved in antibodies.

The 'light chain' of vertebrate antibody (immunoglobulin) could be divided into two distinct types (κ or λ) according to the amino acid sequences of constant region. Based on the amino acid sequences of heavy chain constant region, immune globulins could be divided into different species. There are five classes of immunoglobulins: IgA, IgD, IgE, IgG and IgM, some of them could be further divided into subclass: IgG1, IgG2, IgG3, IgG4, IgA and IgA2. The heavy chain constant regions corresponding to different classes of immunoglobulins could be named as α, δ, ε, γ and μ. The subunit structures and 3D configurations of different immunoglobulins are well known to those skilled in the art.

As used herein, the term 'monoclonal antibody' refers to an antibody obtained from a class of substantially homogeneous population, that is, each antibody of this population is the same except for a few naturally occurring mutations. Monoclonal antibodies are highly specific to a single antigenic site. Additionally, differ from normal polyclonal antibody reagents (which normally possess different antibodies against different determinants), monoclonal antibody is specific to a single determinant. In addition to their specificity, another advantage of monoclonal antibody is that they are synthesized by hybridoma culture technique and are not be polluted by other immunoglobulins. The modifier 'monoclonal' refers to the properties of an antibody that is obtained from a substantially homogeneous population of antibodies and it should not be explained as some special methods are needed to produce the antibody.

The invention also includes a monoclonal antibody having corresponding amino acid sequences of the anti-FcRn protein monoclonal antibody, a monoclonal antibody having the variable region chains of the anti-FcRn protein monoclonal antibody, and other proteins or protein conjugates and fusion expression products having such chains. In particular, the present invention includes any protein or protein conjugate and a fusion expression product (i.e., an immunoconjugate and a fusion expression product) comprising a light chain and a heavy chain containing a variable region as long as the variable region is identical, or at least 90% homologous, preferably at least 95% homologous, with the light chain and heavy chain variable region of the present invention.

As known to those skilled in the art, the immunoconjugates and fusion expression products include conjugates formed by drugs, toxins, cytokines, radionuclides, enzymes and other diagnostic or therapeutic molecules binding to the anti-FcRn protein monoclonal antibody or the fragments thereof of the invention. The present invention also includes cell surface markers or antigens that bind to the anti-FcRn protein monoclonal antibodies or fragments thereof.

The invention not only contains intact monoclonal antibody, but also includes antibody fragments with immunological activity, for instance, Fab or $(Fab')_2$ fragments; antibody heavy chains; antibody light chains.

As used herein, the terms "heavy chain variable region" and "$V_H$" are used interchangeably.

As used herein, the terms "variable region" and "complementary determining region (CDR)" are used interchangeably.

In a preferred embodiment of the invention, the heavy chain variable region of the antibody (FnAb8) comprises three complementary determining regions (CDRs):

CDR1: the amino acid sequence is GYTFTGYY (SEQ ID NO.: 4) and the nucleotide sequence encoding CDR1 is ggatacaccttcaccggctactat (SEQ ID NO.: 3);

CDR2: the amino acid sequence is ISPHSGGT (SEQ ID NO.: 6) and the nucleotide sequence encoding CDR2 is atcagccctcacagtggtggcaca (SEQ ID NO.: 5);

CDR3: the amino acid sequence is ARGVYGMDR (SEQ ID NO.: 8) and the nucleotide sequence encoding CDR3 is gcgcgcggtgtttacggtatggatcgt (SEQ ID NO.: 7);

In a preferred embodiment of the invention, the amino acid sequence of heavy chain variable region is:

```
                                          (SEQ ID NO.: 10)
QVQLVQSGAEVKKPGASVKVSCKTSGYTFTGYYIHWVRQAPGQGLEWMGH
ISPHSGGTDYAQKFQGRVTMTRDTSISTAYMELSRLRSDDTAVYYCARGV
YGMDRWGQGTLVTVSS;
```

The nucleotide sequence encoding $V_H$ is:

```
                                           (SEQ ID NO.: 9)
CAGGTGCAGCTGGTGCAGTCTGGGGCTGAGGTGAAGAAGCCTGGGGCCTC

AGTGAAGGTCTCCTGCAAGACTTCTGGATACACCTTCACCGGCTACTATA

TACACTGGGTGCGACAGGCCCCTGGACAAGGGCTTGAGTGGATGGGACAT

ATCAGCCCTCACAGTGGTGGCACAGACTATGCACAGAAGTTTCAGGGCAG

GGTCACCATGACCAGGGACACGTCCATCAGCACAGCCTACATGGAGCTGA

GCAGGCTGAGATCTGACGACACTGCCGTGTATTACTGTGCGCGCGGTGTT

TACGGTATGGATCGTTGGGGTCAAGGTACTCTGGTGACCGTCTCCTCA.
```

In a preferred embodiment of the invention, the heavy chain of the antibody includes the heavy chain variable region and a heavy chain constant region. The heavy chain constant region could be of human or mouse.

As used herein, the terms "light chain variable region" and "$V_L$" can be used interchangeably.

In a preferred embodiment of the invention, the light chain variable region of the antibody (FnAb8) comprises the complementary determining regions (CDRs) selected from the group of:

CDR1', the amino acid sequence is SSNIGSNS (SEQ ID NO:14), and the nucleotide sequence encoding CDR1' is agctccaacatcggaagtaatagt (SEQ ID NO.:13);

CDR2', the amino acid sequence is SNN (SEQ ID NO:16), and the nucleotide sequence encoding CDR2' is agtaataat (SEQ ID NO.:15)

CDR3', the amino acid sequence is AAWDDSLNGRVL (SEQ ID NO:18), and the nucleotide sequence encoding CDR3' is gcagcgtgggatgacagcctgaatggccgtgtacta (SEQ ID NO.:17).

In a preferred embodiment of the invention, the amino acid sequence of the light chain variable region is:

```
                                          (SEQ ID NO.: 20)
QAVLTQPPSASGTPGQRVTISCSGSSSNIGSNSVNWYQQLPGTAPKLLIY
SNNQRPSGVPDRFSGSKSGTSASLAISGLQSEDEADYYCAAWDDSLNGRV
LFGGGTKLTVL ,
```

The nucleotide sequence encoding $V_L$ is:

```
                                          (SEQ ID NO.: 19)
CAGGCTGTGCTGACTCAGCCACCCTCAGCGTCTGGGACCCCCGGGCAGAG

GGTCACCATCTCTTGTTCTGGAAGCAGCTCCAACATCGGAAGTAATAGTG

TAAACTGGTACCAGCAGCTCCCAGGAACGGCCCCCAAACTCCTCATCTAT

AGTAATAATCAGCGGCCCTCAGGGGTCCCTGACCGATTCTCTGGCTCCAA

GTCTGGCACCTCAGCCTCCCTGGCCATCAGTGGGCTCCAGTCTGAGGATG

AGGCTGATTATTACTGTGCAGCGTGGGATGACAGCCTGAATGGCCGTGTA

CTATTCGGCGGAGGGACCAAGCTGACCGTCCTA.
```

In a preferred embodiment of the invention, the light chain of the antibody includes the above-said light chain variable region and a light chain constant region. The light chain constant region could be of humans or mouse.

In a preferred embodiment of the invention, the heavy chain variable region of the antibody (FnAb12) comprises three complementary determining regions (CDRs):

CDR1, the amino acid sequence is GYTFTSYD (SEQ ID NO:22), and the nucleotide sequence encoding CDR1 is ggatacaccttcaccagttatgat (SEQ ID NO.:21);

CDR2, the amino acid sequence is MNPNSGNT (SEQ ID NO.:24), and the nucleotide sequence encoding CDR2 is atgaaccctaacagtggtaacaca (SEQ ID NO.:23);

CDR3, the amino acid sequence is ARGVDLGDG (SEQ ID NO.:26), and the nucleotide sequence encoding CDR3 is gcgcgcggtgttgacctgggtgatggt (SEQ ID NO.:25).

In a preferred embodiment of the invention, the amino acid sequence of heavy chain variable region is:

```
                                          (SEQ ID NO.: 28)
EVQLVQSGAEVKKPGASVKVSCKASGYTFTSYDINWVRQATGQGLEWMGW
MNPNSGNTGYAQKFQGRVTMTRNTSISTAYMELSSLRSEDTAVYYCARGV
DLGDGWGQGTLVTVSS;
```

The nucleotide sequence encoding $V_H$ is:

```
                                          (SEQ ID NO.: 27)
GAGGTCCAGCTGGTGCAGTCTGGGGCTGAGGTGAAGAAGCCTGGGGCCTC

AGTGAAGGTCTCCTGCAAGGCTTCTGGATACACCTTCACCAGTTATGATA

TCAACTGGGTGCGACAGGCCACTGGACAAGGGCTTGAGTGGATGGGATGG

ATGAACCCTAACAGTGGTAACACAGGCTATGCACAGAAGTTCCAGGGCAG

AGTCACCATGACCAGGAACACCTCCATAAGCACAGCCTACATGGAGCTGA

GCAGCCTGAGATCTGAGGACACGGCCGTGTATTACTGTGCGCGCGGTGTT

GACCTGGGTGATGGTTGGGGTCAAGGTACTCTGGTGACCGTCTCCTCA.
```

In a preferred embodiment of the invention, the heavy chain of the antibody includes the heavy chain variable region and a heavy chain constant region. The heavy chain constant region could be of human or mouse.

As used herein, the terms "light chain variable region" and "$V_L$" are used interchangeably.

In a preferred embodiment of the invention, the light chain variable region of the antibody (FnAb12) comprises the complementary determining regions (CDRs) selected from the group of:

CDR1', the amino acid sequence is QDIDNN (SEQ ID NO:30), and the nucleotide sequence encoding CDR1' is caggacattgacaacaac (SEQ ID NO.:29);

CDR2', the amino acid sequence is DAS (SEQ ID NO:32), and the nucleotide sequence encoding CDR2' is gatgcgtcc (SEQ ID NO.:31);

CDR3', the amino acid sequence is QQYYNLPLT (SEQ ID NO:34), and the nucleotide sequence encoding CDR3' is caacagtattacaatctgcctctgact (SEQ ID NO.:33)

In a preferred embodiment of the invention, the amino acid sequence of the light chain variable region is:

```
                                          (SEQ ID NO.: 36)
DIQLTQSPSSLSASVGDRVTLTCQATQDIDNNLNWYQQKPGKAPKLLIYD
ASNLETGVPSRFSGSGSGTDFTFTISDLQPEDVATYYCQQYYNLPLTFGG
GTKVDIK
```

The nucleotide sequence encoding $V_L$ is:

```
                                          (SEQ ID NO.: 35)
GACATCCAGTTGACCCAGTCTCCATCCTCCCTGTCTGCATCCGTTGGCGA

CAGAGTCACCCTCACTTGCCAGGCGACTCAGGACATTGACAACAACTTAA

ATTGGTATCAACAAAAGCCGGGGAAAGCCCCTAAGCTCCTGATCTACGAT

GCGTCCAATTTGGAAACAGGAGTCCCGTCACGGTTCAGCGGGAGTGGATC

TGGGACAGATTTTACTTTCACCATTAGTGACCTACAGCCTGAAGATGTTG

CAACATATTACTGTCAACAGTATTACAATCTGCCTCTGACTTTCGGCGGA

GGGACCAAAGTGGATATCAAA
```

In a preferred embodiment of the invention, the light chain of the antibody includes the above-said light chain variable region and a light chain constant region. The light chain constant region could be of human or mouse.

In the present invention, the terms "antibody of the present invention", "protein of the present invention" or "polypeptide of the present invention" are used interchangeably and all refer to polypeptides that specifically bind to FcRn protein, for example, a protein or polypeptide comprising a heavy chain variable region (e.g. SEQ ID NO.: 10 amino acid sequence) and/or a light chain variable region (e.g. SEQ ID NO.: 20 amino acid sequence). They may or may not contain a starting methionine.

In a preferred embodiment of the invention, the antibody is a mouse or human-mouse chimeric monoclonal antibody against FcRn protein and their heavy chain constant region and/or light chain constant region could be humanized heavy chain constant region or light chain constant region. Preferably, the humanized heavy chain constant region or light chain constant region are the heavy chain constant region or light chain constant region of human IgG2, IgG2 and etc.

The present invention also provides other proteins or fusion expression products having the antibodies of the present invention. In particular, the present invention includes any protein or protein conjugate and fusion expression products (i.e., an immunoconjugate and a fusion expression product) comprising a heavy chain and a light chain containing a variable region as long as the variable region is identical, or at least 90% homologous, preferably at least 95% homologous, with the heavy chain and light chain variable region of the antibody of the present invention.

In general, the antigen-binding properties of an antibody can be described by three specific regions located in the heavy chain and light chain variable region, referring as variable regions (CDRs), and this segment is separated into four framework regions (FRs). The sequences of four FRs amino acids are relatively conservative and do not directly participate in the binding reaction. A cyclic structure are formed by these CDRs, β-folds formed by the FRs between them are close to each other in the spatial structure, and the CDRs on the heavy chains and the CDRs on the corresponding light chains constitute the antigen-binding sites of the antibody. The amino acid sequence of the same type of antibody can be used to determine which amino acids have constituted the FR or CDR region.

The variable regions of the heavy chains and/or light chains of the antibodies of the invention are of particular interest, because at least parts of them are involved in binding to an antigen. Thus, the invention encompasses those molecules having an monoclonal antibody heavy chain and light chain variable region with CDRs as long as their CDRs have a homology of more than 90% (preferably more than 95%, optimally more than 98%) to the CDRs identified herein.

The present invention includes not only intact antibodies but also fragments of antibodies or fusion proteins formed by antibodies with other sequences with immunological activity. Accordingly, the present invention also includes fragments, derivatives and analogs of said antibodies.

As used herein, the terms "fragments", "derivatives" and "analogs" refer to the polypeptides that substantially maintain the same biological function or activity of the antibodies of the present invention. The polypeptide fragments, derivatives or analogs of the present invention may be (i) a polypeptide with one or more conservative or non-conservative amino acid residues (preferably the conservative amino acid residues) being substituted, while such a substituted amino acid residue may or may not be encoded by a genetic code, or (ii) a polypeptide having substituted group(s) in one or more amino acid residues, or (iii) a polypeptide formed by fusion of the mature polypeptide with another compound (such as the compound that prolongs the half life of the polypeptide, such as polyethylene glycol), or (iv) a polypeptide with additional amino acid sequence fused to said polypeptide sequence (such as fusion proteins formed by fusion with leader sequence, secretion sequence or sequence used to purify the polypeptide or proprotein sequence, or a fusion protein formed with a 6His tag. According to the teachings of the present application, these fragments, derivatives and analogs are within the scope commonly known by the skilled person.

An antibody of the present invention refers to a polypeptide comprising the CDRs regions and having FcRn protein binding activity. The term also includes a variant form of the polypeptide comprising the above CDRs regions and having the same function as the antibodies of the present invention. These variations include (but are not limited to) deletion, insert and/or substitution of one or more (typically 1-50, preferably 1-30, more preferably 1-20, most preferably 1-10) amino acids, and adding one or more (typically 20 or less, preferably 10 or less, more preferably 5 or less) amino acids at the C-terminus and/or N-terminus. For example, in the art, substitution with similar or similar amino acids does not usually alter the function of the protein. Also, for example, the addition of one or several amino acids at the C-terminus and/or the N-terminus will not usually alter the function of the protein. The term also includes the active fragments and active derivatives of the antibodies of the present invention.

The mutated forms of the polypeptide include homologous sequences, conserved variants, allelic variants, natural mutants, induced mutants, proteins encoded by DNA that hybridizes to the encoded DNA of the antibodies of the present invention under high or low stringency conditions, and polypeptides or proteins obtained using antisera against antibodies of the present invention.

The present invention also provides other polypeptides, such as fusion proteins comprising a human antibody or a fragment thereof. In addition to the substantially full length polypeptides, the present invention also encompasses fragments of antibodies of the present invention. Typically, the fragment has at least about 50 consecutive amino acids of the antibody of the present invention, preferably at least about 60 consecutive amino acids, more preferably at least about 80 consecutive amino acids, and most preferably at least about 100 consecutive amino acids.

In the present invention, the "conserved variants of the antibodies of the present invention" refers to the polypeptides formed by substituting at most 10, preferably at most 8, more preferably at most 5, and most preferably 3 amino acid of the amino acid sequence of the polypeptide of the present invention with the amino acid having similar or analogous properties. These conservative variant polypeptides are preferably formed by carrying out the amino acid substitution according to Table 1.

TABLE 1

| Initial residue | Representative substitution | Preferred substitution |
|---|---|---|
| Ala (A) | Val; Leu; Ile | Val |
| Arg (R) | Lys; Gln; Asn | Lys |
| Asn (N) | Gln; His; Lys; Arg | Gln |
| Asp (D) | Glu | Glu |
| Cys (C) | Ser | Ser |
| Gln (Q) | Asn | Asn |
| Glu (E) | Asp | Asp |
| Gly (G) | Pro; Ala | Ala |
| His (H) | Asn; Gln; Lys; Arg | Arg |
| Ile (I) | Leu; Val; Met; Ala; Phe | Leu |
| Leu (L) | Ile; Val; Met; Ala; Phe | Ile |
| Lys (K) | Arg; Gln; Asn | Arg |
| Met (M) | Leu; Phe; Ile | Leu |
| Phe (F) | Leu; Val; Ile; Ala; Tyr | Leu |
| Pro (P) | Ala | Ala |
| Ser (S) | Thr | Thr |
| Thr (T) | Ser | Ser |
| Trp (W) | Tyr; Phe | Tyr |
| Tyr (Y) | Trp; Phe; Thr; Ser | Phe |
| Val (V) | Ile; Leu; Met; Phe; Ala | Leu |

The present invention also provides a polynucleotide molecule encoding the above antibody or a fragment thereof or a fusion protein thereof. The polynucleotides of the present invention can be in a form of DNA or RNA. DNA includes cDNA, genomic DNA, or synthetic DNA. DNA may be single-stranded or double-stranded. DNA may be the coding strand or non-coding strand. The sequences of coding regions for coding mature polypeptides could have same sequences or degenerate variants of SEQ ID NO.: 3, 5, 7, 9, 13, 15, 17 and 19. As used herein the term 'degenerate variant' in the present invention refers to nucleic acid sequences encoding the same amino acid sequence with the polypeptides of the present invention but different with the coding regions of SEQ ID NO.: 3, 5, 7, 9, 13, 15, 17 and 19.

The polynucleotide encoding the mature polypeptide of the present invention includes coding sequences encoding only mature polypeptides; coding sequences of mature polypeptides and various additional coding sequences; coding sequences (and optional additional coding sequences) of mature polypeptides and non-coding sequences.

The term "polynucleotide encoding the polypeptide" may be a polynucleotide that encodes the polypeptide, or a polynucleotide that also includes additional coding and/or non-coding sequences.

The present invention also relates to a polynucleotide that hybridize to the sequence described above and that have at least 50%, preferably at least 70%, more preferably at least 80% identity between the two sequences. In particular, the present invention relates to a polynucleotide that is hybridizable to the polynucleotide of the present invention under stringent conditions. In the present invention, "stringent conditions" means: (1) hybridization and elution at lower ionic strength and higher temperature, such as 0.2×SSC, 0.1% SDS, 60° C.; or (2) hybridization in the presence of a denaturant such as 50% (v/v) formamide, 0.1% calf serum/0.1% Ficoll, 42° C. or the like; or (3) hybridization occurs only if the identity between the two sequences is at least 90%, more preferably 95% or more. And the polypeptide encoded by the hybridizable polynucleotide has the same biological function and activity as the mature polypeptide shown in one of SEQ ID NO: 10 and/or SEQ ID NO.: 20.

The full-length nucleotide sequence of the present invention or a fragment thereof can usually be obtained by PCR amplification methods, recombination methods or synthetic methods. A viable approach is to synthesize the relevant sequence by synthetic methods, especially when the length of the fragment is short. In general, a very long fragment can be obtained by first synthesizing multiple small fragments and then ligating them. In addition, the coding sequence of the heavy chain and the expression tag (e.g., 6His) can be fused together to form a fusion protein.

Once the relevant sequence is obtained, the relevant sequence can be obtained in bulk using the recombination method. It is usually cloned into a vector, transferred to a cell, and then isolated from the host cell after proliferation by conventional methods. The biomolecules (nucleic acids, proteins, etc.) involved in the present invention include biomolecules existing in separate forms.

At present, DNA sequences encoding the protein of the present invention (or fragments thereof, or derivatives thereof) can be completely obtained by chemical synthesis. Then the DNA sequence can be introduced into a variety of current DNA molecules (or vectors) and cells known in the art. In addition, mutations can also be introduced into the protein sequences of the present invention by chemical synthesis.

The present invention also relates to vectors comprising the suitable DNA sequence as described above and a suitable promoter or control sequence. These vectors can be used to transform suitable host cells to enable them to express proteins.

Host cells can be prokaryotic cells, such as bacterial cells; or lower eukaryotic cells, such as yeast cells; or higher eukaryotic cells, such as mammalian cells. Representative examples include: bacterial cells such as *Escherichia coli, Streptomyces; Salmonella typhimurium*; fungal cells such as yeast; insect cells such as *Drosophila* S2 or Sf 9; animal cells such as CHO, COS7, 293 cells, etc.

Transformation of host cells with recombinant DNA can be carried out using conventional techniques well known to those skilled in the art. When the host is a prokaryote such as *E. coli*, competent cells capable of absorbing DNA can be harvested after the exponential growth phase and treated with the $CaCl_2$. The steps used are well known in the art. Another method is using $MgCl_2$. If necessary, the transformation can also be carried out by electroporation. When the host is a eukaryote, the following DNA transfection methods are available: calcium phosphate coprecipitation, conventional mechanical methods such as microinjection, electroporation, liposome packaging, and the like.

The obtained transformants can be cultured by conventional methods to express the polypeptides encoded by the genes of the present invention. Depending on the host cell used, the medium used in the culture may be selected from a variety of conventional media. And the host cells are cultured under conditions suitable for the growth. After the host cells grow to appropriate cell density, the selected promoter is induced with a suitable method, such as temperature conversion or chemical induction, and the cells are cultured for a further period of time.

The recombinant polypeptide in the above method can be expressed intracellularly, or on the cell membrane, or secreted out of the cell. If desired, recombinant proteins can be isolated and purified by various separation methods using their physical, chemical and other properties. These methods are well known to those skilled in the art. Examples of such methods include, but are not limited to, conventional renaturation treatments, treatment with a protein precipitant (salting-out method), centrifugation, penetration-breaking bacteria, super-treatment, ultracentrifugation, molecular sieve chromatography (gel filtration), adsorption chromatography, ion-exchange chromatography, high performance liquid chromatography (HPLC) and various other liquid chromatography techniques and combinations of these methods.

The antibodies of the present invention may be used alone or in combination with or coupling with a detectable label (for diagnostic purposes), a therapeutic agent, a PK (protein kinase) modified moiety, or any combination thereof.

A detectable label for diagnostic purposes include, but are not limited to, fluorescent or luminescent labels, radiolabels, MRI (magnetic resonance imaging), or CT (computerized tomography) contrast agents, or enzymes capable of producing detectable products.

Conjugable therapeutic agent include, but are not limited to, insulin, IL-2, interferon, calcitonin, GHRH peptide, gut peptide analog, albumin, antibody fragments, cytokines, and hormones, etc.

Further therapeutic agents that can be combined with or coupled with the antibodies of the present invention include, but are not limited to: 1. Radioactive nuclide (Koppe, et al, 2005, *Cancer metastasis reviews* 24, 539); 2. Biological toxin (Chaudhary et al, 1989, *Nature,* 339, 394; Epel et al, 2002, *Cancer immunology and immunotherapy* 51,565); 3. Cytokine such as IL-2 and the like (Gillies, et al, 1992, PNAS, 89,1428; Card, et al, 2004, *Cancer immunology and immunotherapy* 53, 345; Halin, et al, 2003, *Cancer research* 63, 3202); 4. Gold nano-particle/nano-rod (Lapotko, et al, 2005, *Cancer letters* 239, 36; Huang, et al, 2006, *Journal of the American chemical society* 128, 2115); 5. Virus particles (Peng, et al, 2004, *Gene therapy,* 11, 1234); 6. Liposome (Mamot, et al, 2005, *Cancer research* 65,11631); 7. Magnetic nano-particles; 8. Prodrug activating enzymes (such as DT-diaphorase (DTD) or Biphenyl hydrolase-like protein (BPHL)); 10. Chemotherapeutic agent (e.g., cisplatin) or any form of nanoparticles and the like.

The present invention also provides a composition. In a preferred embodiment, the composition is a pharmaceutical composition comprising the above-described antibody or active fragment thereof or a fusion protein thereof, and a pharmaceutically acceptable carrier. In general, these materials may be formulated in a non-toxic, inert and pharmaceutically acceptable aqueous carrier medium, wherein the pH is generally about 5 to 8, preferably about 6 to 8, although the pH may vary depending on the nature of the substance to be formulated, and the condition to be treated. The formulated pharmaceutical compositions may be administered by conventional routes, including, but not limited to, oral, respiratory, intratumoral, intraperitoneal, intravenous, or local drug delivery.

The pharmaceutical compositions of the present invention can be used directly to bind with FcRn protein molecules and are therefore useful for prolonging the half-life of drugs. In addition, other therapeutic agents may be used at the same time.

The pharmaceutical composition of the present invention contains a monoclonal antibody (or a conjugate thereof) of the present invention in a safe and effective amount (e.g., 0.001 to 99 wt %, preferably 0.01 to 90 wt %, more preferably 0.1 to 80 wt %) and a pharmaceutically acceptable carrier or excipient. Such carriers include, but are not limited to, saline, buffer, glucose, water, glycerol, ethanol, and combinations thereof. The pharmaceutical preparation should match the method of administration. The pharmaceutical compositions of the present invention may be prepared into the form of injections, for example, it is prepared by conventional methods using physiological saline or aqueous solutions containing glucose and other adjuvants. Pharmaceutical compositions such as injections, solutions should be prepared under aseptic conditions. The amount of the active ingredient is a therapeutically effective amount, such as about 1 microgram/kg body weight per day to about 10 mg/kg body weight per day. In addition, the polypeptides of the present invention may also be used with other therapeutic agents.

When a pharmaceutical composition is used, a safe and effective amount of an immunoconjugate is administered to a mammal wherein the safe effective amount is generally at least about 10 micrograms per kilogram of body weight and, in most cases, no more than about 8 milligrams per kilogram of body weight, preferably, the dose is from about 10 micrograms per kilogram body weight to about 1 milligram per kilogram of body weight. Of course, the route of administration, the patient's health status and other factors, should be considered for the specific dose, which are within the scope of skills of skilled practitioners.

The Main Advantages of the Present Invention Include:

(1) The monoclonal antibodies provided by the present invention have a significantly higher affinity for binding to FcRn at weakly acidic pH, compared with IgG and SA; while maintaining a weak affinity at neutral pH, which is similar to IgG and SA; and they are more effective, compared with IgG and SA, in recycling in vivo using FcRn, thereby significantly prolonging their half-life;

(2) The monoclonal antibody of the present invention has a significant pH-dependent binding to FcRn and can be used as a drug carrier. After being coupled or recombinantly expressed with a polypeptide, a protein or other drugs, patient compliance can be improved while administration dose and frequency of drugs and drug cost can be reduced by way of prolonging the half-life of drugs;

(3) The monoclonal antibody of the present invention can be used for preparing a single chain antibody or a double chain antibody, and being conjugated or recombinantly expressed with a drug molecule. Since the single chain antibody and the double chain antibody have a small molecular weight, they can be expressed by a non-mammalian cell system, thereby simplifying the production process and reducing production costs;

(4) The monoclonal antibody provided by the present invention can be a human antibody and needs no further humanization.

The present invention will be further illustrated below with reference to the specific examples. It should be understood that these examples are only to illustrate the invention, not to limit the scope of the invention. The experimental methods with no specific conditions described in the following examples are generally performed under the conventional conditions (e.g., the conditions described by US Sambrook et al., Molecular Cloning Laboratory Guide (Huang Peitang et al., Beijing: Science Press, 2002), or according to the manufacture's instructions. Unless indicated otherwise, all percentage and parts are calculated by weight. Unless otherwise stated, the experimental materials and reagents used in the following examples are available from commercially available sources.

Unless otherwise stated, the experimental materials used in the examples of the present invention are available from commercially available sources. Among them, hIgG, HLA-A2 protein was purchased from invitrogen; b2M, GLP-1R-Fc was purchased from Sino Biological Inc.; Luciferase assay kits and detecting instruments were purchased from Promega; Avidin-coated ELISA plate was purchased from invitrogen; Biotin labeling kit was purchased from Solulink; Instruments for the detection of plasma surface resonance technology, buffers, consumables, etc. are all purchased from GE Healthcare; The hFcRn&b2M protein for detection, the EGFP-FnRn cell line expressing hFcRn&b2M, and the EGFP-HLA-A2 cell line expressing HLA-A2&b2M were prepared according to references 2 and 3 by the inventors. The remaining universal cell culture and transfection reagents were purchased from invitrogen and chemical reagents were purchased from Sigma.

EXAMPLE 1

Generation and Screening of Monoclonal Antibody

In the present Example, single chain antibody phage library was screened as shown in FIG. 1. Firstly, b2M and hFcRn&b2M were biotinylated, and then the biotinylated b2M was mixed with the phage antibody library. Upon subtraction screening, phages to binding to b2M were removed using streptavidin-coupled magnetic beads. The supernatant was mixed with biotinylated hFcRn&b2M protein, and the phages binding to hFcRn were collected with magnetic beads, and amplified for the next round of panning. After 3 rounds of panning, single phage clones were picked out for amplification and positive phages were identified by phage enzyme-linked immunosorbent assay and sequenced. The gene was cloned into a new expression vector to express the antibody, which was purified and subjected to subsequent identification of binding, affinity, and the like.

Figure 2:
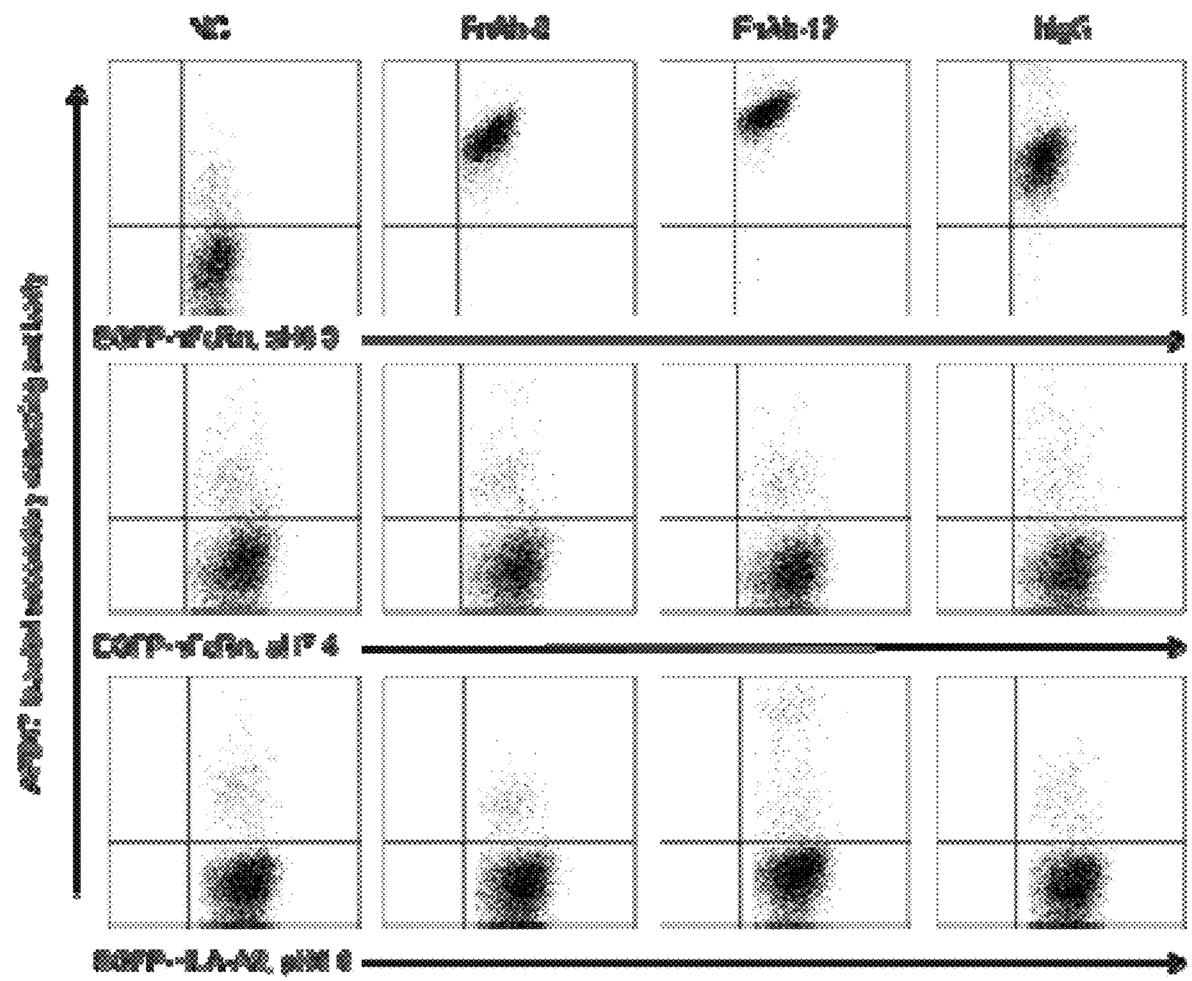
FIG. 2 shows typical FCM (flow cytometry) results, demonstrating that the selected phage clones bind to hFcRn&$\beta_2$M or HLA-A2&$\beta_2$M at pH 6 and pH 7.4 on cell surface.

Through subtractive panning at different pH (pH6.0/pH7.4), two single chain antibodies, FnAb8 and FnAb12, have been identified, which can specifically recognize human FcRn protein with high affinity and binding constant is significantly pH-dependent. As shown in table 1, at pH 6.0, their binding affinities are 100-200 folds higher than that of wild type hIgG and SA, while they exhibited similar affinity to hFcRn at pH7.4 (>10 uM), as compared with wild type hIgG and SA. Similar to IgG, the binding of the single-chain antibodies to FcRn is pH-dependent at cellular level. The results showed that the specificity and pH dependence of FnAb8 and FnAb12 binding to FcRn were detected using HEK293 cell line expressing hFcRn&b2M and control cell line expressing HLA-A2&b2M. In particular, FnAb8 and FnAb12, like hIgG, did not bind to HEK293 cells expressing HLA-A2, did not bind to HEK293 cells expressing hFcRn at neutral pH, and FnAb8 and FnAb12 can specifically bind to cell-expressed hFcRn only at weakly acidic pH, while negative control antibody (NC) did not bind to HLA-A2 or hFcRn. FIG. 2 shows a typical FCM (flow cytometry) results, demonstrating binding of selected phage clones to hFcRn & β2M or HLA-A2 & β2M at pH 6.0 and pH 7.4. As shown in FIG. 2, FnAb8, like hIgG, did not bind to HEK293 cells expressing HLA-A2 (lower layer) and did not bind to HEK293 cells expressing hFcRn at neutral pH (in the middle layer), and FnAb8 can specifically bind to hFcRn expressed by cells (upper layer) only at weakly acidic pH, while negative control antibody (NC) did not bind to HLA-A2 or hFcRn.

TABLE 1

Binding affinity of FnAb8 and FnAb12 to hFcRn

| Ligand | Sample | KD (pH 6.0) | KD (pH 7.4) |
|---|---|---|---|
| hFcRn & b2M | FnAb8 | 2.62E−09 | >10 uM |
| hFcRn & b2M | FnAb12 | 1.50E−08 | >10 uM |

FnAb8 and FnAb12 antibodies were sequenced and analyzed by routine methods in the art, and results are shown as below:

| FnAb8 | SEQ ID NO.: | FnAb12 | SEQ ID NO.: |
|---|---|---|---|
| HC CDR1 | 4 | HC CDR1 | 22 |
| HC CDR2 | 6 | HC CDR2 | 24 |
| HC CDR3 | 8 | HC CDR3 | 26 |
| HC variable region | 10 | HC variable region | 28 |
| LC CDR1 | 14 | LC CDR1 | 30 |
| LC CDR2 | 16 | LC CDR2 | 32 |
| LC CDR3 | 18 | LC CDR3 | 34 |
| LC variable region | 20 | LC variable region | 36 |

EXAMPLE 2

Generation of Fusion Protein

A nucleotide sequence expressing GLP1 (7-36 amino acids, containing three mutation sites, A8G, G22E, and R36G) was ligated to 5' end of a nucleotide sequence of FnAb8 or FnAb12 with a (G4S)3 linker, and the gene was synthesized and inserted into expression vector pcDNA3.1 (Jinsley Biotechnology Co., Ltd.). And then the plasmid was transfected into mammalian cells to prepare a protein.

Below is the amino acid sequence of GLP1 protein (AA7-36):

(SEQ ID NO.: 2)
HGEGTFTSDVSSYLEEQAAKEFIAWLVKGG

In the present example, GLP1 (AA7-36) was successfully fusion-expressed with two single-chain antibodies respectively, thereby obtaining fusion proteins. The fusion protein obtained by fusion expression with FnAb8 was named as G8, and the fusion protein obtained by fusion expression with FnAb12 was named as G12.

The amino acid sequence of fusion protein G8:

(SEQ ID NO.: 11)
HGEGTFTSDVSSYLEEQAAKEFIAWLVKGGGGGGGSGGGGSGGGGSQAVLTQPPSASGTPGQRVTISCSGSSSNIGSNSVNWYQQLPGTAPKLLIYSNNQRPSGVPDRFSGSKSGTSASLAISGLQSEDEADYYCAAWDDSLNGRVLFGGGTKLTVLGSRGGGGSGGGGSGGGGSLEMAQVQLVQSGAEVKKPGASVKVSCKTSGYTFTGYYIHWVRQAPGQGLEWMGHISPHSGGTDYAQKFQGRVTMTRDTSISTAYMELSRLRSDDTAVYYCARGVYGMDRWGQGTLVTVSS, the underlined is the single chain antibody sequence.

The amino acid sequence of fusion protein G12:

(SEQ ID NO.: 12)
HGEGTFTSDVSSYLEEQAAKEFIAWLVKGGGGGGGSGGGGSGGGGSDIQLTQSPSSLSASVGDRVTLTCQATQDIDNNLNWYQQKPGKAPKLLIYDASNLETGVPSRFSGSGSGTDFTFTISDLQPEDVATYYCQQYYNLPLTFGGGTKVDIKRSRGGGGSGGGGSGGGGSLEMAEVQLVQSGAEVKKPGASVKVSCKASGYTFTSYDINWVRQATGQGLEWMGWMNPNSGNTGYAQKFQGRVTMTRNTSISTAYMELSSLRSEDTAVYYCARGVDLGDGWGQGTLVTVSS, the underlined is the single chain antibody sequence.

EXAMPLE 3

In-Vitro Activity Test of Fusion Proteins

The binding between GLP1 fusion protein and its corresponding receptor protein, was identified using Surface Plasma Resonance (SPR) technology. GLP-1R-Fc protein and hIgG were immobilized on a CM5 chip by chemical coupling using Biacore T100, and 200 nM of FnAb8, G8, FnAb12 and G12 were flowed through the surface of the chip at high speed respectively to detect binding signals.

Biacore was used to identify the binding of GLP-1 fusion protein to hFcRn. hFcRn was coupled to a CM5 chip, and 200 nM of FnAb8, G8, FnAb12 and G12 were flowed through the surface of the chip at high speed to detect the binding signals.

Figure 3:
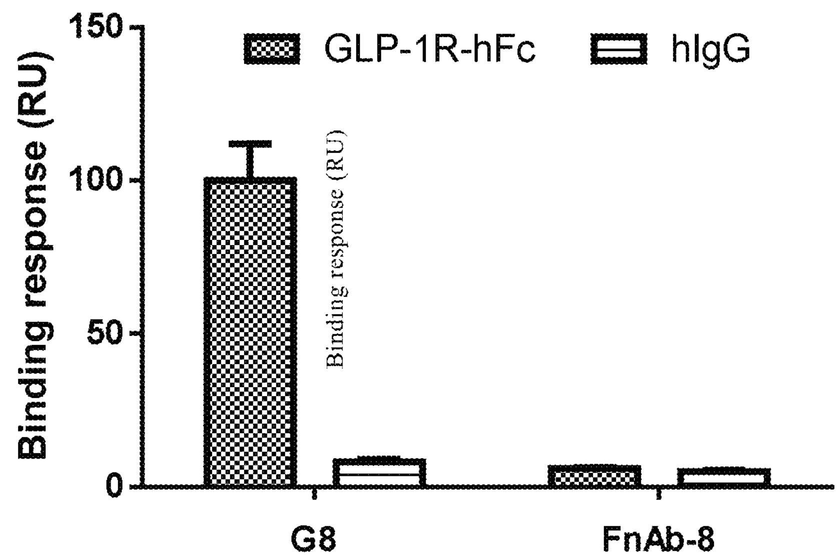
FIG. 3 shows G8 binding to GLP-1R-Fc. GLP-1R-Fc or hIgG was immobilized on CM5 chip, and 200 nM of G8, FnAb8 flowed over the chip surface at high speed to detect bindings between G8, FnAb8 and GLP-1R-Fc and hIgG Fc.
Figure 4:
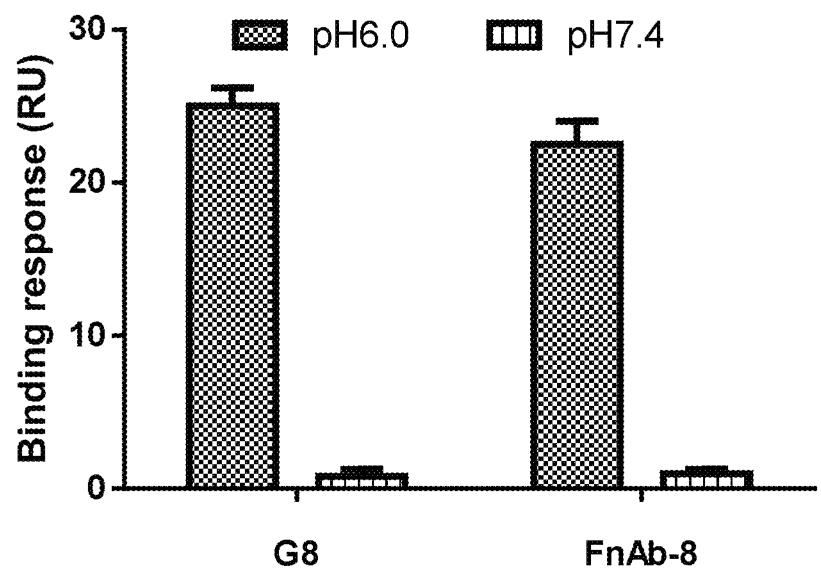
FIG. 4 shows G8 binding to hFcRn. hFcRn&$\beta_2$M was immobilized on CM5 chip, and 200 nM G8, FnAb8 flowed over the chip surface at high speed to detect bindings between G8, FnAb8 and hFcRn at pH6.0 or pH7.4.

The experimental results of the present example demonstrated that G8 and G12 can specifically bind to GLP-1R. Both of G8 and G12 can bind to FcRn protein and maintain the pH-dependence of binding. FIG. 3 shows the binding of G8 to GLP-1R-Fc protein. GLP-1R-Fc or hIgG was coupled to a CM5 chip, and 200 nM of G8, FnAb8 was flowed through the surface of the chip at high speed to detect their binding to GLP-1R-Fc and hIgG Fc. FIG. 4 shows the binding of G8 to hFcRn protein. hFcRn&β2M was immobilized on a CM5 chip, and 200 nM of G8 and FnAb8 were flowed through the surface of the chip at high speed to detect their binding to hFcRn at pH 6.0 and pH 7.4.

EXAMPLE 4

Cellular Activity Test of Fusion Protein

The CRE-Luc/GLP-1R HEK293 cell line was used to identify the cellular biological activity of GLP-1 fusion protein. Briefly, CRE-Luc/GLP-1R HEK293 cells were seeded into 96 well cell culture plate at $5\times10^4$/well and cultured overnight. Next day, serially diluted G8 or G12 solution was added to the cell culture plate. After cultured for 5 hours, the cells were washed twice with PBS, and then lysed with cell lysis liquid, and luciferase activity was detected by using Luciferase assay kit (Promega). Binding of GLP-1 to GLP-1R expressed on the cell surface will stimulate the production of cAMP, thereby inducing the expression of Luciferase, the activity of which will be proportional to the binding strength of GLP-1 and its receptor. The binding activity of GLP-1 to GLP-1R can be determined by measuring the activity of Luciferase.

Figure 5:
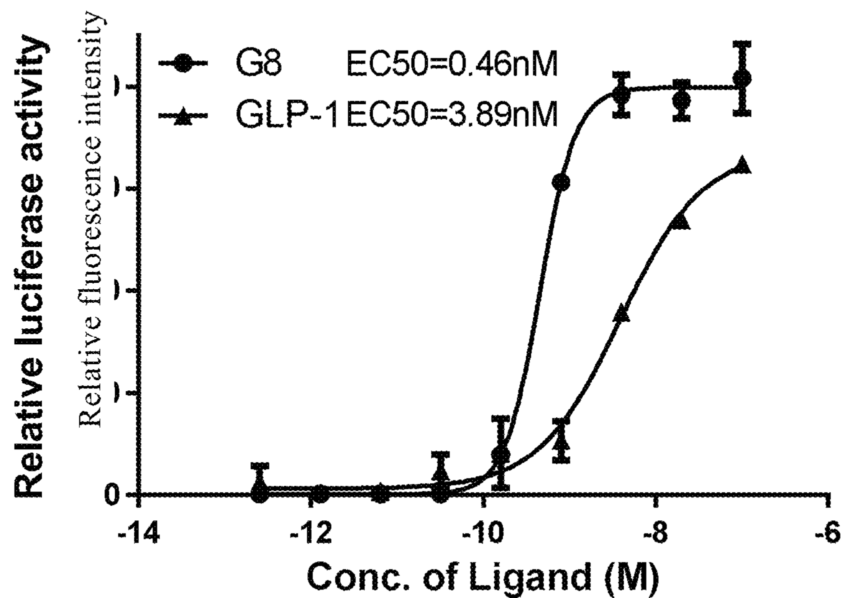
FIG. 5 shows effects of G8 on HEK293/CRE-Luc/GLP-1R cells.

The results showed that the binding activity of G8 and G12 to GLP-1R was dose-dependent, and its EC50 was almost comparable to that of the reported GLP-1 polypeptide, demonstrating that the fusion protein retained the biological activity of GLP-1 and had comparable efficacy. FIG. 5 shows the effects of G8 on HEK293/CRE-Luc/GLP-1R cells.

EXAMPLE 5

Biological Activity Experiment In-Vivo

Figure 6:
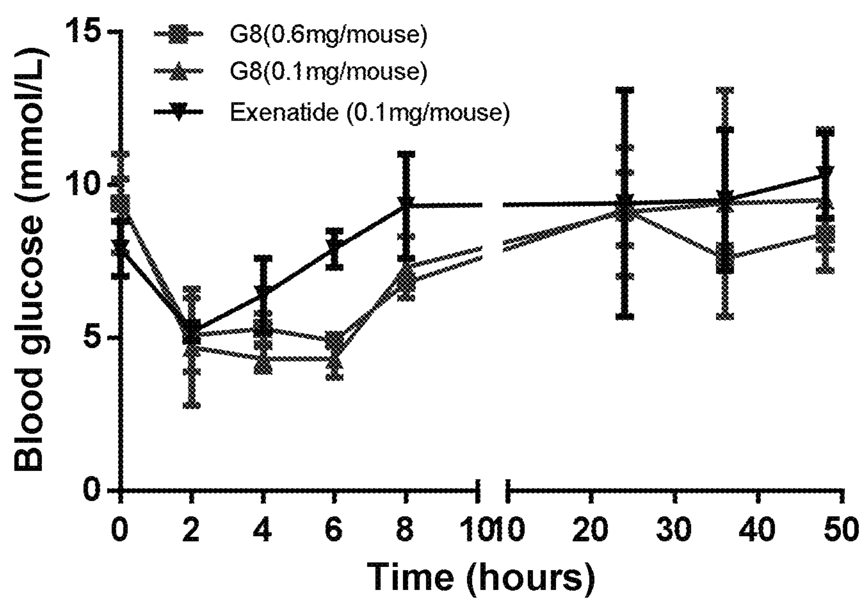
FIG. 6 shows the therapeutical effects of lowering blood glucose levels in Diet-induced Diabetis mice models.

Male C57BL/6 mice (7 weeks old) were purchased from JOINN Laboratory Inc (Suzhou, J S), all of which were fed either standard rodent chow (SRC) or a high-fat diet (HFD, 45% kcal from fat; Medicience Inc, Yangzhou, J S) for 18 days. Obese mice with 20% weight and 30% blood glucose increase as compared with those SRC fed were randomized into 3 groups with 3 mice in each group (n=3) and given subcutaneous (SC) injection of G8, G12, or Exenatide (0.1 mg/mouse), blood glucose changes in mice were determined at various time points by blood glucose meter. Experiment results showed that G8 and G12 had significant blood glucose lowering effects and the duration of the drug was significantly longer than that of Exenatide. FIG. 6 shows in vivo hypoglycemic effects on a diet-induced Diabetes mouse model.

EXAMPLE 6

In-Vivo Half-Life Determination

Two healthy female cynomolgus monkeys (purchased from Guangxi Changchun Biotechnology Co., Ltd., average age 6.5-7 years; body weight 3.3 kg) were selected, and given biotinylated FnAb8 antibody, 1 mg/kg body weight through tail vein injection. Plasma samples (~2 ml) were taken at 0, 0.5, 6, 24, 48, 96, 240, 408, 576, 744, 1008 hours. The blood concentration of FnAb8 was detected by sandwich method with a plate pre-coated with avidin, and analyzed by WinNonlin software. The obtained results of pharmacokinetic study are shown in Table 2. The average residence time in vivo of the FnAb8 antibody was 240 hours or so (half-life of 204 and 98 hours, respectively), while almost all single-chain antibodies have a half-life of only a few minutes to several hours in vivo. The half-life of FnAb8 is tens to hundreds of times that of a typical single-chain antibody.

TABLE 2

| Pharmacokinetic data of FnAb in cynomolgus macaque | | | | |
|---|---|---|---|---|
| ID | β phase $T_{1/2}$(h) | $AUC_{inf}$(ug*h/ml) | Cl_F(ml/h/kg) | MRT (h) |
| Cyno-1 | 204 | 2084 | 0.48 | 273 |
| Cyno-2 | 98 | 2200 | 0.45 | 204 |

B phase $T_{1/2}$(h): elimination half life;
$AUC_{inf}$(ug*h/ml): area under the plasma concentration curve;
Cl_F(ml/h/kg): clear rate;
MRT(h): mean residence time Summing up, the two novel single-chain antibody sequences of the present invention have specificity, high affinity and pH-dependent binding to hFcRn, and upon fusion expression with functional proteins, their own binding trait can be maintained while the biological function of the fusion protein can also be maintained. And in vivo studies have shown that the single-chain antibodies have a longer half-life, so that the two new antibodies have great potential for the development of biopharmaceuticals with extended half-life.

All the documents cited herein are incorporated into the invention as reference, as if each of them is individually incorporated. Further, it would be appreciated that, in light of the above described teaching of the invention, the skilled in the art could make various changes or modifications to the invention, and these equivalents would still be in the scope of the invention defined by the appended claims of the application.

REFERENCES

[1] M. Raghavan, V. R. Bonagura, S. L. Morrison, P. J. Bjorkman, Analysis of the pH dependence of the neonatal Fc receptor/immunoglobulin G interaction using antibody and receptor variants, Biochemistry. 34 (1995) 14649-14657. doi:10.1021/bi00045a005.

[2] R. L. Shields, A. K. Namenuk, K. Hong, Y. G. Meng, J. Rae, J. Briggs, et al., High Resolution Mapping of the Binding Site on Human IgG1 for Fc□RI, Fc□RII, Fc□RIII, and FcRn and Design of IgG1 Variants with Improved Binding to the Fc□R, J. Biol. Chem. 276 (2001) 6591-6604. doi:10.1074/jbc.M009483200.

G. J. Christianson, V. Z. Sun, S. Akilesh, E. Pesavento, G. Proetzel, D. C. Roopenian, Monoclonal antibodies directed against human FcRn and their applications, MAbs. 4 (2012) 208-216. doi:10.4161/mabs.4.2.19397.

The invention claimed is:

1. An anti-human FcRn antibody, or a fusion protein thereof or an immunoconjugate thereof, wherein the antibody has a heavy chain and a light chain, wherein the heavy chain has a heavy chain variable region having the following three complementary determining regions (CDRs):

CDR1 as shown in SEQ ID NO: 4,

CDR2 as shown in SEQ ID NO: 6 and

CDR3 as shown in SEQ ID NO: 8;

and the light chain has a light chain variable region having the following three complementary determining regions (CDRs):

CDR1' as shown in SEQ ID NO: 14,

CDR2' as shown in SEQ ID NO: 16, and

CDR3' as shown in SEQ ID NO: 18;

or wherein the heavy chain has a heavy chain variable region having the following three complementary determining regions (CDRs):

CDR1 as shown in SEQ ID NO: 22,

CDR2 as shown in SEQ ID NO: 24 and

CDR3 as shown in SEQ ID NO: 26;

and the light chain has a light chain variable region having the following three complementary determining regions (CDRs):

CDR1' as shown in SEQ ID NO: 30,

CDR2' as shown in SEQ ID NO: 32, and

CDR3' as shown in SEQ ID NO: 34.

2. The antibody of claim 1, wherein the heavy chain further has a heavy chain constant region and the light chain further has a light chain constant region.

3. The antibody of claim 2, wherein the heavy chain constant region is of human or mouse; and the light chain constant region is of human or mouse.

4. The antibody of claim 1, wherein the antibody comprises a single chain antibody (scFv), a double chain antibody, a monoclonal antibody, a chimeric antibody, a murine antibody or a humanized antibody.

5. The antibody of claim 1, wherein the heavy chain variable region has the amino acid sequence as shown in SEQ ID NO: 10; and the light chain variable region has the amino acid sequence as shown in SEQ ID NO: 20.

6. The antibody of claim 1, wherein the heavy chain variable region has the amino acid sequence as shown in SEQ ID NO: 28; and the light chain variable region has the amino acid sequence as shown in SEQ ID NO: 36.

7. The antibody of claim 1, or a fusion protein thereof or an immunoconjugate thereof wherein the immunoconjugate comprises:

(a) the antibody; and (b) a coupling moiety selected from the group consisting of a detectable label, a drug, a toxin, a cytokine, a radionuclide, and an enzyme.

8. The antibody of claim 7, or a fusion protein thereof or an immunoconjugate thereof, wherein the coupling moiety is GLP1 peptide or a fragment thereof.

9. The antibody of claim 7, or a fusion protein thereof or an immunoconjugate thereof, wherein the coupling moiety is a peptide as shown in SEQ ID No. 2.

10. A pharmaceutical composition which comprises:

(i) an antibody of claim 1, or a fusion protein thereof, or an immunoconjugate thereof; and (ii) a pharmaceutically acceptable carrier.

11. The pharmaceutical composition of claim 10, which is in the form of an injection.

12. The pharmaceutical composition of claim 10, wherein the fusion protein has the amino acid sequence as shown in SEQ ID No. 11.

13. The pharmaceutical composition of claim 10, wherein the fusion protein has the amino acid sequence as shown in SEQ ID No. 12.

14. The antibody of claim 1 wherein the antibody is a single chain antibody (scFv).

15. The antibody of claim 1 wherein the antibody binds specifically to the human FcRn in a pH-dependent manner.

* * * * *

SEQUENCE LISTING

```
<160> NUMBER OF SEQ ID NOS: 36

<210> SEQ ID NO 1
<211> LENGTH: 365
<212> TYPE: PRT
<213> ORGANISM: Homo sapiens
```

<400> SEQUENCE: 1

Met Gly Val Pro Arg Pro Gln Pro Trp Ala Leu Gly Leu Leu Leu Phe
1 5 10 15

Leu Leu Pro Gly Ser Leu Gly Ala Glu Ser His Leu Ser Leu Leu Tyr
20 25 30

His Leu Thr Ala Val Ser Ser Pro Ala Pro Gly Thr Pro Ala Phe Trp
35 40 45

Val Ser Gly Trp Leu Gly Pro Gln Gln Tyr Leu Ser Tyr Asn Ser Leu
50 55 60

Arg Gly Glu Ala Glu Pro Cys Gly Ala Trp Val Trp Glu Asn Gln Val
65 70 75 80

Ser Trp Tyr Trp Glu Lys Glu Thr Thr Asp Leu Arg Ile Lys Glu Lys
85 90 95

Leu Phe Leu Glu Ala Phe Lys Ala Leu Gly Gly Lys Gly Pro Tyr Thr
100 105 110

Leu Gln Gly Leu Leu Gly Cys Glu Leu Gly Pro Asp Asn Thr Ser Val
115 120 125

Pro Thr Ala Lys Phe Ala Leu Asn Gly Glu Glu Phe Met Asn Phe Asp
130 135 140

Leu Lys Gln Gly Thr Trp Gly Gly Asp Trp Pro Glu Ala Leu Ala Ile
145 150 155 160

Ser Gln Arg Trp Gln Gln Gln Asp Lys Ala Ala Asn Lys Glu Leu Thr
165 170 175

Phe Leu Leu Phe Ser Cys Pro His Arg Leu Arg Glu His Leu Glu Arg
180 185 190

Gly Arg Gly Asn Leu Glu Trp Lys Glu Pro Pro Ser Met Arg Leu Lys
195 200 205

Ala Arg Pro Ser Ser Pro Gly Phe Ser Val Leu Thr Cys Ser Ala Phe
210 215 220

Ser Phe Tyr Pro Pro Glu Leu Gln Leu Arg Phe Leu Arg Asn Gly Leu
225 230 235 240

Ala Ala Gly Thr Gly Gln Gly Asp Phe Gly Pro Asn Ser Asp Gly Ser
245 250 255

Phe His Ala Ser Ser Ser Leu Thr Val Lys Ser Gly Asp Glu His His
260 265 270

Tyr Cys Cys Ile Val Gln His Ala Gly Leu Ala Gln Pro Leu Arg Val
275 280 285

Glu Leu Glu Ser Pro Ala Lys Ser Ser Val Leu Val Val Gly Ile Val
290 295 300

Ile Gly Val Leu Leu Leu Thr Ala Ala Ala Val Gly Gly Ala Leu Leu
305 310 315 320

Trp Arg Arg Met Arg Ser Gly Leu Pro Ala Pro Trp Ile Ser Leu Arg
325 330 335

Gly Asp Asp Thr Gly Val Leu Leu Pro Thr Pro Gly Glu Ala Gln Asp
340 345 350

Ala Asp Leu Lys Asp Val Asn Val Ile Pro Ala Thr Ala
355 360 365

<210> SEQ ID NO 2
<211> LENGTH: 30
<212> TYPE: PRT
<213> ORGANISM: Artificial sequence
<220> FEATURE:
<223> OTHER INFORMATION: Polypeptide

<400> SEQUENCE: 2

His Gly Glu Gly Thr Phe Thr Ser Asp Val Ser Ser Tyr Leu Glu Glu
1 5 10 15

Gln Ala Ala Lys Glu Phe Ile Ala Trp Leu Val Lys Gly Gly
20 25 30

<210> SEQ ID NO 3
<211> LENGTH: 24
<212> TYPE: DNA
<213> ORGANISM: Artificial sequence
<220> FEATURE:
<223> OTHER INFORMATION: Polynucleotide

<400> SEQUENCE: 3
ggatacacct tcaccggcta ctat 24

<210> SEQ ID NO 4
<211> LENGTH: 8
<212> TYPE: PRT
<213> ORGANISM: Artificial sequence
<220> FEATURE:
<223> OTHER INFORMATION: Polypeptide

<400> SEQUENCE: 4

Gly Tyr Thr Phe Thr Gly Tyr Tyr
1 5

<210> SEQ ID NO 5
<211> LENGTH: 24
<212> TYPE: DNA
<213> ORGANISM: Artificial sequence
<220> FEATURE:
<223> OTHER INFORMATION: Polynucleotide

<400> SEQUENCE: 5
atcagccctc acagtggtgg caca 24

<210> SEQ ID NO 6
<211> LENGTH: 8
<212> TYPE: PRT
<213> ORGANISM: Artificial sequence
<220> FEATURE:
<223> OTHER INFORMATION: Polypeptide

<400> SEQUENCE: 6

Ile Ser Pro His Ser Gly Gly Thr
1 5

<210> SEQ ID NO 7
<211> LENGTH: 27
<212> TYPE: DNA
<213> ORGANISM: Artificial sequence
<220> FEATURE:
<223> OTHER INFORMATION: Polynucleotide

<400> SEQUENCE: 7
gcgcgcggtg tttacggtat ggatcgt 27

<210> SEQ ID NO 8
<211> LENGTH: 9
<212> TYPE: PRT
<213> ORGANISM: Artificial sequence
<220> FEATURE:
<223> OTHER INFORMATION: Polypeptide

<400> SEQUENCE: 8

```
Ala Arg Gly Val Tyr Gly Met Asp Arg
1               5
```

<210> SEQ ID NO 9
<211> LENGTH: 348
<212> TYPE: DNA
<213> ORGANISM: Artificial sequence
<220> FEATURE:
<223> OTHER INFORMATION: Polynucleotide

<400> SEQUENCE: 9

```
caggtgcagc tggtgcagtc tggggctgag gtgaagaagc ctggggcctc agtgaaggtc      60

tcctgcaaga cttctggata caccttcacc ggctactata tacactgggt gcgacaggcc     120

cctggacaag ggcttgagtg gatgggacat atcagccctc acagtggtgg cacagactat     180

gcacagaagt ttcagggcag ggtcaccatg accagggaca cgtccatcag cacagcctac     240

atggagctga gcaggctgag atctgacgac actgccgtgt attactgtgc gcgcggtgtt     300

tacggtatgg atcgttgggg tcaaggtact ctggtgaccg tctcctca                 348
```

<210> SEQ ID NO 10
<211> LENGTH: 116
<212> TYPE: PRT
<213> ORGANISM: Artificial sequence
<220> FEATURE:
<223> OTHER INFORMATION: Polypeptide

<400> SEQUENCE: 10

```
Gln Val Gln Leu Val Gln Ser Gly Ala Glu Val Lys Lys Pro Gly Ala
1               5                   10                  15

Ser Val Lys Val Ser Cys Lys Thr Ser Gly Tyr Thr Phe Thr Gly Tyr
            20                  25                  30

Tyr Ile His Trp Val Arg Gln Ala Pro Gly Gln Gly Leu Glu Trp Met
        35                  40                  45

Gly His Ile Ser Pro His Ser Gly Gly Thr Asp Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Val Tyr Gly Met Asp Arg Trp Gly Gln Gly Thr Leu Val
            100                 105                 110

Thr Val Ser Ser
        115
```

<210> SEQ ID NO 11
<211> LENGTH: 295
<212> TYPE: PRT
<213> ORGANISM: Artificial sequence
<220> FEATURE:
<223> OTHER INFORMATION: Polypeptide

<400> SEQUENCE: 11

```
His Gly Glu Gly Thr Phe Thr Ser Asp Val Ser Ser Tyr Leu Glu Glu
1               5                   10                  15

Gln Ala Ala Lys Glu Phe Ile Ala Trp Leu Val Lys Gly Gly Gly Gly
            20                  25                  30

Gly Gly Gly Ser Gly Gly Gly Gly Ser Gly Gly Gly Gly Ser Gln Ala
        35                  40                  45
```

```
Val Leu Thr Gln Pro Pro Ser Ala Ser Gly Thr Pro Gly Gln Arg Val
    50                  55                  60

Thr Ile Ser Cys Ser Gly Ser Ser Ser Asn Ile Gly Ser Asn Ser Val
65                  70                  75                  80

Asn Trp Tyr Gln Gln Leu Pro Gly Thr Ala Pro Lys Leu Leu Ile Tyr
                85                  90                  95

Ser Asn Asn Gln Arg Pro Ser Gly Val Pro Asp Arg Phe Ser Gly Ser
            100                 105                 110

Lys Ser Gly Thr Ser Ala Ser Leu Ala Ile Ser Gly Leu Gln Ser Glu
        115                 120                 125

Asp Glu Ala Asp Tyr Tyr Cys Ala Ala Trp Asp Asp Ser Leu Asn Gly
    130                 135                 140

Arg Val Leu Phe Gly Gly Gly Thr Lys Leu Thr Val Leu Gly Ser Arg
145                 150                 155                 160

Gly Gly Gly Gly Ser Gly Gly Gly Gly Ser Gly Gly Gly Gly Ser Leu
                165                 170                 175

Glu Met Ala Gln Val Gln Leu Val Gln Ser Gly Ala Glu Val Lys Lys
            180                 185                 190

Pro Gly Ala Ser Val Lys Val Ser Cys Lys Thr Ser Gly Tyr Thr Phe
        195                 200                 205

Thr Gly Tyr Tyr Ile His Trp Val Arg Gln Ala Pro Gly Gln Gly Leu
    210                 215                 220

Glu Trp Met Gly His Ile Ser Pro His Ser Gly Gly Thr Asp Tyr Ala
225                 230                 235                 240

Gln Lys Phe Gln Gly Arg Val Thr Met Thr Arg Asp Thr Ser Ile Ser
                245                 250                 255

Thr Ala Tyr Met Glu Leu Ser Arg Leu Arg Ser Asp Asp Thr Ala Val
            260                 265                 270

Tyr Tyr Cys Ala Arg Gly Val Tyr Gly Met Asp Arg Trp Gly Gln Gly
        275                 280                 285

Thr Leu Val Thr Val Ser Ser
    290                 295


<210> SEQ ID NO 12
<211> LENGTH: 291
<212> TYPE: PRT
<213> ORGANISM: Artificial sequence
<220> FEATURE:
<223> OTHER INFORMATION: Polypeptide

<400> SEQUENCE: 12

His Gly Glu Gly Thr Phe Thr Ser Asp Val Ser Ser Tyr Leu Glu Glu
1               5                   10                  15

Gln Ala Ala Lys Glu Phe Ile Ala Trp Leu Val Lys Gly Gly Gly Gly
            20                  25                  30

Gly Gly Gly Ser Gly Gly Gly Gly Ser Gly Gly Gly Gly Ser Asp Ile
        35                  40                  45

Gln Leu Thr Gln Ser Pro Ser Ser Leu Ser Ala Ser Val Gly Asp Arg
    50                  55                  60

Val Thr Leu Thr Cys Gln Ala Thr Gln Asp Ile Asp Asn Asn Leu Asn
65                  70                  75                  80

Trp Tyr Gln Gln Lys Pro Gly Lys Ala Pro Lys Leu Leu Ile Tyr Asp
                85                  90                  95

Ala Ser Asn Leu Glu Thr Gly Val Pro Ser Arg Phe Ser Gly Ser Gly
            100                 105                 110
```

```
Ser Gly Thr Asp Phe Thr Phe Thr Ile Ser Asp Leu Gln Pro Glu Asp
        115                 120                 125

Val Ala Thr Tyr Tyr Cys Gln Gln Tyr Tyr Asn Leu Pro Leu Thr Phe
    130                 135                 140

Gly Gly Gly Thr Lys Val Asp Ile Lys Arg Ser Arg Gly Gly Gly Gly
145                 150                 155                 160

Ser Gly Gly Gly Gly Ser Gly Gly Gly Gly Ser Leu Glu Met Ala Glu
                165                 170                 175

Val Gln Leu Val Gln Ser Gly Ala Glu Val Lys Lys Pro Gly Ala Ser
            180                 185                 190

Val Lys Val Ser Cys Lys Ala Ser Gly Tyr Thr Phe Thr Ser Tyr Asp
        195                 200                 205

Ile Asn Trp Val Arg Gln Ala Thr Gly Gln Gly Leu Glu Trp Met Gly
    210                 215                 220

Trp Met Asn Pro Asn Ser Gly Asn Thr Gly Tyr Ala Gln Lys Phe Gln
225                 230                 235                 240

Gly Arg Val Thr Met Thr Arg Asn Thr Ser Ile Ser Thr Ala Tyr Met
                245                 250                 255

Glu Leu Ser Ser Leu Arg Ser Glu Asp Thr Ala Val Tyr Tyr Cys Ala
            260                 265                 270

Arg Gly Val Asp Leu Gly Asp Gly Trp Gly Gln Gly Thr Leu Val Thr
        275                 280                 285

Val Ser Ser
    290


<210> SEQ ID NO 13
<211> LENGTH: 24
<212> TYPE: DNA
<213> ORGANISM: Artificial sequence
<220> FEATURE:
<223> OTHER INFORMATION: Polynucleotide

<400> SEQUENCE: 13

agctccaaca tcggaagtaa tagt                                            24


<210> SEQ ID NO 14
<211> LENGTH: 8
<212> TYPE: PRT
<213> ORGANISM: Artificial sequence
<220> FEATURE:
<223> OTHER INFORMATION: Polypeptide

<400> SEQUENCE: 14

Ser Ser Asn Ile Gly Ser Asn Ser
1               5


<210> SEQ ID NO 15
<211> LENGTH: 9
<212> TYPE: DNA
<213> ORGANISM: Artificial sequence
<220> FEATURE:
<223> OTHER INFORMATION: Polynucleotide

<400> SEQUENCE: 15

agtaataat                                                              9


<210> SEQ ID NO 16
<211> LENGTH: 3
<212> TYPE: PRT
<213> ORGANISM: Artificial sequence
```

<220> FEATURE:
<223> OTHER INFORMATION: Polypeptide

<400> SEQUENCE: 16

Ser Asn Asn
1

<210> SEQ ID NO 17
<211> LENGTH: 36
<212> TYPE: DNA
<213> ORGANISM: Artificial sequence
<220> FEATURE:
<223> OTHER INFORMATION: Polynucleotide

<400> SEQUENCE: 17
gcagcgtggg atgacagcct gaatggccgt gtacta 36

<210> SEQ ID NO 18
<211> LENGTH: 12
<212> TYPE: PRT
<213> ORGANISM: Artificial sequence
<220> FEATURE:
<223> OTHER INFORMATION: Polypeptide

<400> SEQUENCE: 18

Ala Ala Trp Asp Asp Ser Leu Asn Gly Arg Val Leu
1 5 10

<210> SEQ ID NO 19
<211> LENGTH: 333
<212> TYPE: DNA
<213> ORGANISM: Artificial sequence
<220> FEATURE:
<223> OTHER INFORMATION: Polynucleotide

<400> SEQUENCE: 19
caggctgtgc tgactcagcc accctcagcg tctgggaccc ccgggcagag ggtcaccatc 60
tcttgttctg gaagcagctc caacatcgga agtaatagtg taaactggta ccagcagctc 120
ccaggaacgg cccccaaact cctcatctat agtaataatc agcggccctc aggggtccct 180
gaccgattct ctggctccaa gtctggcacc tcagcctccc tggccatcag tgggctccag 240
tctgaggatg aggctgatta ttactgtgca gcgtgggatg acagcctgaa tggccgtgta 300
ctattcggcg gagggaccaa gctgaccgtc cta 333

<210> SEQ ID NO 20
<211> LENGTH: 111
<212> TYPE: PRT
<213> ORGANISM: Artificial sequence
<220> FEATURE:
<223> OTHER INFORMATION: Polypeptide

<400> SEQUENCE: 20

Gln Ala Val Leu Thr Gln Pro Pro Ser Ala Ser Gly Thr Pro Gly Gln
1 5 10 15

Arg Val Thr Ile Ser Cys Ser Gly Ser Ser Ser Asn Ile Gly Ser Asn
20 25 30

Ser Val Asn Trp Tyr Gln Gln Leu Pro Gly Thr Ala Pro Lys Leu Leu
35 40 45

Ile Tyr Ser Asn Asn Gln Arg Pro Ser Gly Val Pro Asp Arg Phe Ser
50 55 60

Gly Ser Lys Ser Gly Thr Ser Ala Ser Leu Ala Ile Ser Gly Leu Gln
65 70 75 80

```
Ser Glu Asp Glu Ala Asp Tyr Tyr Cys Ala Ala Trp Asp Asp Ser Leu
                85                  90                  95

Asn Gly Arg Val Leu Phe Gly Gly Gly Thr Lys Leu Thr Val Leu
            100                 105                 110


<210> SEQ ID NO 21
<211> LENGTH: 24
<212> TYPE: DNA
<213> ORGANISM: Artificial sequence
<220> FEATURE:
<223> OTHER INFORMATION: Polynucleotide

<400> SEQUENCE: 21

ggatacacct tcaccagtta tgat                                            24


<210> SEQ ID NO 22
<211> LENGTH: 8
<212> TYPE: PRT
<213> ORGANISM: Artificial sequence
<220> FEATURE:
<223> OTHER INFORMATION: Polypeptide

<400> SEQUENCE: 22

Gly Tyr Thr Phe Thr Ser Tyr Asp
1               5


<210> SEQ ID NO 23
<211> LENGTH: 24
<212> TYPE: DNA
<213> ORGANISM: Artificial sequence
<220> FEATURE:
<223> OTHER INFORMATION: Polynucleotide

<400> SEQUENCE: 23

atgaacccta acagtggtaa caca                                            24


<210> SEQ ID NO 24
<211> LENGTH: 8
<212> TYPE: PRT
<213> ORGANISM: Artificial sequence
<220> FEATURE:
<223> OTHER INFORMATION: Polypeptide

<400> SEQUENCE: 24

Met Asn Pro Asn Ser Gly Asn Thr
1               5


<210> SEQ ID NO 25
<211> LENGTH: 27
<212> TYPE: DNA
<213> ORGANISM: Artificial sequence
<220> FEATURE:
<223> OTHER INFORMATION: Polynucleotide

<400> SEQUENCE: 25

gcgcgcggtg ttgacctggg tgatggt                                         27


<210> SEQ ID NO 26
<211> LENGTH: 9
<212> TYPE: PRT
<213> ORGANISM: Artificial sequence
<220> FEATURE:
<223> OTHER INFORMATION: Polypeptide

<400> SEQUENCE: 26
```

```
Ala Arg Gly Val Asp Leu Gly Asp Gly
1               5


<210> SEQ ID NO 27
<211> LENGTH: 348
<212> TYPE: DNA
<213> ORGANISM: Artificial sequence
<220> FEATURE:
<223> OTHER INFORMATION: Polynucleotide

<400> SEQUENCE: 27

gaggtccagc tggtgcagtc tggggctgag gtgaagaagc ctggggcctc agtgaaggtc     60

tcctgcaagg cttctggata caccttcacc agttatgata tcaactgggt gcgacaggcc    120

actggacaag ggcttgagtg gatgggatgg atgaacccta acagtggtaa cacaggctat    180

gcacagaagt tccagggcag agtcaccatg accaggaaca cctccataag cacagcctac    240

atggagctga gcagcctgag atctgaggac acggccgtgt attactgtgc gcgcggtgtt    300

gacctgggtg atggttgggg tcaaggtact ctggtgaccg tctcctca                348


<210> SEQ ID NO 28
<211> LENGTH: 116
<212> TYPE: PRT
<213> ORGANISM: Artificial sequence
<220> FEATURE:
<223> OTHER INFORMATION: Polypeptide

<400> SEQUENCE: 28

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Asp Ile Asn Trp Val Arg Gln Ala Thr Gly Gln Gly Leu Glu Trp Met
        35                  40                  45

Gly Trp Met Asn Pro Asn Ser Gly Asn Thr Gly Tyr Ala Gln Lys Phe
    50                  55                  60

Gln Gly Arg Val Thr Met Thr Arg Asn Thr Ser Ile Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Val Asp Leu Gly Asp Gly Trp Gly Gln Gly Thr Leu Val
            100                 105                 110

Thr Val Ser Ser
        115


<210> SEQ ID NO 29
<211> LENGTH: 18
<212> TYPE: DNA
<213> ORGANISM: Artificial sequence
<220> FEATURE:
<223> OTHER INFORMATION: Polynucleotide

<400> SEQUENCE: 29

caggacattg acaacaac                                                   18


<210> SEQ ID NO 30
<211> LENGTH: 6
<212> TYPE: PRT
<213> ORGANISM: Artificial sequence
<220> FEATURE:
<223> OTHER INFORMATION: Polypeptide
```

<400> SEQUENCE: 30

Gln Asp Ile Asp Asn Asn
1 5

<210> SEQ ID NO 31
<211> LENGTH: 9
<212> TYPE: DNA
<213> ORGANISM: Artificial sequence
<220> FEATURE:
<223> OTHER INFORMATION: Polynucleotide

<400> SEQUENCE: 31 gatgcgtcc 9

<210> SEQ ID NO 32
<211> LENGTH: 3
<212> TYPE: PRT
<213> ORGANISM: Artificial sequence
<220> FEATURE:
<223> OTHER INFORMATION: Polypeptide

<400> SEQUENCE: 32

Asp Ala Ser
1

<210> SEQ ID NO 33
<211> LENGTH: 27
<212> TYPE: DNA
<213> ORGANISM: Artificial sequence
<220> FEATURE:
<223> OTHER INFORMATION: Polynucleotide

<400> SEQUENCE: 33
caacagtatt acaatctgcc tctgact 27

<210> SEQ ID NO 34
<211> LENGTH: 9
<212> TYPE: PRT
<213> ORGANISM: Artificial sequence
<220> FEATURE:
<223> OTHER INFORMATION: Polypeptide

<400> SEQUENCE: 34

Gln Gln Tyr Tyr Asn Leu Pro Leu Thr
1 5

<210> SEQ ID NO 35
<211> LENGTH: 321
<212> TYPE: DNA
<213> ORGANISM: Artificial sequence
<220> FEATURE:
<223> OTHER INFORMATION: Polynucleotide

<400> SEQUENCE: 35
gacatccagt tgacccagtc tccatcctcc ctgtctgcat ccgttggcga cagagtcacc 60
ctcacttgcc aggcgactca ggacattgac aacaacttaa attggtatca acaaaagccg 120
gggaaagccc ctaagctcct gatctacgat gcgtccaatt tggaaacagg agtcccgtca 180
cggttcagcg ggagtggatc tgggacagat tttactttca ccattagtga cctacagcct 240
gaagatgttg caacatatta ctgtcaacag tattacaatc tgcctctgac tttcggcgga 300
gggaccaaag tggatatcaa a 321

<210> SEQ ID NO 36

```
<211> LENGTH: 107
<212> TYPE: PRT
<213> ORGANISM: Artificial sequence
<220> FEATURE:
<223> OTHER INFORMATION: Polypeptide

<400> SEQUENCE: 36

Asp Ile Gln Leu Thr Gln Ser Pro Ser Ser Leu Ser Ala Ser Val Gly
1               5                   10                  15

Asp Arg Val Thr Leu Thr Cys Gln Ala Thr Gln Asp Ile Asp Asn Asn
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Phe Thr Ile Ser Asp Leu Gln Pro
65                  70                  75                  80

Glu Asp Val Ala Thr Tyr Tyr Cys Gln Gln Tyr Tyr Asn Leu Pro Leu
                85                  90                  95

Thr Phe Gly Gly Gly Thr Lys Val Asp Ile Lys
            100                 105
```